US005113854A

United States Patent [19]

[11] Patent Number: 5,113,854

[45] Date of Patent: May 19, 1992

Dosch et al.

[54] QUICK-DONNING PROTECTIVE HOOD ASSEMBLY

[75] Inventors: Jeffrey J. Dosch, Buffalo; James V. Zappa, Williamsville, both of N.Y.

[73] Assignee: Figgie International, Inc., Willoughby, Ohio

[21] Appl. No.: 470,066

[22] Filed: Jan. 25, 1990

[51] Int. Cl.[5] ...................... A62B 17/04; A62B 18/00; A62B 7/10; A61M 15/00

[52] U.S. Cl. .......................... 128/201.23; 128/202.26; 128/205.22; 128/201.25; 128/205.27

[58] Field of Search ...................... 128/201.22, 201.23, 128/201.24, 201.25, 202.26, 205.22, 205.27

[56] References Cited

U.S. PATENT DOCUMENTS

| | | | |
|---|---|---|---|
| 3,080,587 | 3/1963 | Steinke | 128/201.23 |
| 3,292,617 | 12/1966 | McDonough | 128/202.26 |
| 3,482,568 | 12/1969 | Bovard | 128/202.26 |
| 3,577,988 | 5/1971 | Jones | 128/201.25 |
| 3,591,343 | 7/1971 | McGoff et al. | 128/202.26 |
| 3,762,407 | 10/1973 | Shonerd | 128/201.23 |
| 4,164,218 | 8/1979 | Martin | 128/202.26 |
| 4,221,216 | 9/1980 | Kranz | 128/201.23 |
| 4,231,359 | 11/1980 | Martin | 128/201.18 |
| 4,236,514 | 12/1980 | Moretti | 128/201.23 |
| 4,552,140 | 11/1985 | Cowley et l. | 128/201.25 |
| 4,559,939 | 12/1985 | Levine et al. | 128/201.25 |
| 4,619,254 | 10/1986 | Moretti | 128/201.23 |
| 4,627,431 | 12/1986 | Werjefelt | 128/201.25 |
| 4,757,813 | 7/1988 | Haydu | 128/201.26 |
| 4,766,893 | 8/1988 | Drews | 128/201.23 |
| 4,807,614 | 2/1989 | van der Smissen et al. | 128/201.23 |
| 4,836,197 | 6/1989 | Röhling et al. | 128/201.23 |
| 4,889,113 | 12/1989 | Pelloux-Gervais et al. | 128/201.25 |
| 4,896,665 | 1/1990 | Gervais | 128/201.25 |

FOREIGN PATENT DOCUMENTS 2164570 3/1986 United Kingdom .

*Primary Examiner*—Edgar S. Burr
*Assistant Examiner*—Kimberly L. Asher
*Attorney, Agent, or Firm*—Hodgson, Russ, Andrews, Woods & Goodyear

[57] ABSTRACT

A quick-donning protective hood assembly for respiratory protection from smoke and noxious gases. The assembly consists of a clear "TEFLON" film hood (12) having a scrubber canister (20) and an exhaust valve (42) supported thereon. A neck seal (14) is connected to the lower marginal edge of the hood. A springlike hoop (16) is connected to the lower marginal edge of the hood. A bib (18) is carried by the springlike hoop and supports an oxygen generator (22) which is interconnected with the scrubber canister by an oxygen supply line (24). Waist straps (54) extend from the sides of the bib and may be adjusted to secure the bib about the wearer. The assembly can be stored in a cylindrical storage container with the hoop being collapsed. When the assembly is withdrawn from the storage container, a lanyard (62) will initiate the operation of the chemical oxygen generator. In addition, chemiluminescent devices (64) are secured to the hoop when in the storage container, and the springing open of the hoop when withdrawn from the storage container will initiate a chemiluminescent reaction within the illuminating devices. The springlike hoop will additionally spring the assembly open to position the components for quick donning.

7 Claims, 3 Drawing Sheets

QUICK-DONNING PROTECTIVE HOOD ASSEMBLY

TECHNICAL FIELD

The present invention relates generally to breathing devices, and more particularly to a quick-donning protective hood assembly for respiratory protection from smoke and noxious gases. The hood assembly of this invention may be used by aircraft passengers.

BACKGROUND OF THE INVENTION

In many situations it may be desirable to provide individuals with protective hood assemblies for respiratory protection from smoke and noxious gases. For example, in an aircraft it may be desirable to provide each passenger with a device which will protect the passenger from fires within the passenger compartment and which will also protect the passenger should the aircraft lose pressure at high altitude. Various such devices are well known in the prior art. A mask typically is provided in today's commercial aircraft, which mask can be strapped to the passenger's face, the mask in turn being connected to a source of oxygen carried by the aircraft. While these devices generally function satisfactorily in their intended manner, they are not designed for fire protection. Thus, if there is a fire within the compartment of the aircraft, it is possible with today's typical masks that toxic gases can be inhaled. This is most likely to happen if the wearer has a beard. The smoke from the fire will also typically cause skin and eye irritation. Severe eye irritation may, of course, interfere with one's ability to see. In addition, today's passenger compartment masks may not be utilized when exiting from the aircraft as no means are provided either for recycling the exhaled gases or for providing the mask with oxygen once the passenger leaves the area of his or her seat.

Prior art escape breathing apparatus has been proposed which will provide oxygen and some protection from smoke. One such example is shown in Swedish Patent 448,681. Another example is shown in U.S. Pat. No. 2,048,059. Both of these patents disclose the use of a protective hood, an oxygen supply interconnected with the hood, and a carbon-dioxide scrubber. However, the apparatus shown in both patents would appear to be somewhat difficult to don, particularly during night time if there is no available lighting. Furthermore, each of these devices would require the operator to initiate the flow of oxygen. It has been found that many passengers in an aircraft are incapable of following relatively simple instructions during an emergency situation, and therefore, it is desirable that the operation of any protective equipment be initiated either through the removal of the equipment from storage or through the donning process. In addition, the apparatus should be designed in such a manner that it is relatively easy to don.

OBJECTS AND SUMMARY OF THE INVENTION

It is an object of the present invention to provide a protective hood assembly for respiratory protection from smoke and noxious gas which is self-contained and which may be readily donned.

More particularly, it is an object of the present invention to provide a self-contained closed-circuit breathing assembly designed to protect an aircraft passenger from the harmful effects of smoke and toxic gases during an in-flight or ground emergency, which assembly may also provide oxygen to the passenger in the event of loss of cabin pressure during flight.

It is a further object of the present invention to provide a self-contained closed-circuit breathing assembly which may be stored in a collapsed fashion, the operation of which assembly commences when the assembly is withdrawn from the storage container, the assembly further providing full peripheral vision when worn.

It is a further object of the present invention to provide a quick-donning protective hood assembly including a clear "TEFLON" hood providing a full peripheral vision, which assembly will accommodate beards and glasses, and which will protect the wearer in an oxygen-deficient atmosphere or during decompression of a passenger compartment during flight of an aircraft, the device being completely self-contained to allow unrestricted mobility, which will be quick-donning with minimal training and which will additionally be provided with its own light source, the initiation of the operation of the light source taking place as the assembly is withdrawn from its storage container.

In accordance with the present invention the assembly consists of a clear "TEFLON" film hood having a scrubber canister and an exhaust valve supported thereon, the hood terminating in a lower open marginal edge, there being a neck seal connected to the lower marginal edge, and wherein a springlike hoop is connected to the open lower marginal edge. A bib is carried by the springlike hoop and supports an oxygen generator which is interconnected with the scrubber canister by an oxygen supply line. Waist straps extend from the sides of the bib and may be used to secure the bib about the wearer. The assembly can be stored in a cylindrical storage container with the hoop being collapsed. A lanyard will initiate the operation of the chemical-oxygen generator when the assembly is withdrawn from the container. In addition, the assembly is provided with one or more chemiluminescent devices, preferably in the form of light sticks secured to the neck hoop, which chemiluminescent devices will be caused to become operative at the same time the protective hood assembly is withdrawn from the storage container. The springlike hoop will spring the assembly open to position the components for quick donning.

The foregoing will become more apparent after a consideration of the following detailed description taken in conjunction with the accompanying drawings in which a preferred form of this invention is illustrated.

DETAILED DESCRIPTION

Figure 1A:
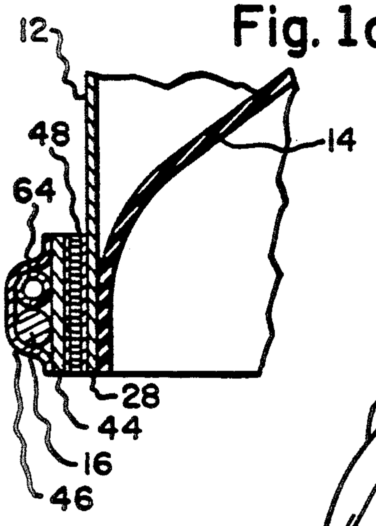
FIGS. 1*a* and 1*b* are sectional views taken generally along the lines 1*a*—1*a* and 1*b*—1*b*, respectively, in FIG. 1.
Figure 1B:
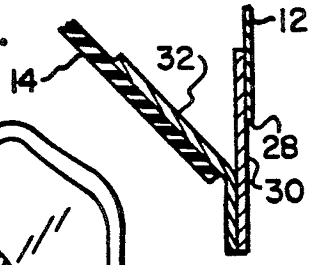

The quick-donning protective hood assembly of this invention is indicated generally at 10. It includes, as its major components, a hood 12, a neck seal 14, a springlike neck hoop interconnected with the hood and neck seal, and a bib 18 supported by the neck hoop. A scrubber canister 20 is carried by the hood 12 and an oxygen generator 22 is carried by the bib 18, the canister and generator being interconnected by an oxygen supply line 24. The hood 12 is preferably made from a clear "TEFLON" film. "TEFLON" is a preferred material because of its high heat resistance, high oxygen index, and excellent optical clarity. The hood is preferably made from a single sheet of "TEFLON" film; the sheet being formed into a hoodlike shape and heat sealed along the seam 26. The hood 12 terminates at its lower edge in an open lower marginal edge portion 28 (FIG. 1*b*). The upper portion of a coated fabric tape 30 is heat sealed to the lower marginal edge portion 28 of the hood. An outer surface portion of the urethane film strip 32 is heat sealed to the lower inner portion of tape 30. The neck seal 14 is formed from a neoprene foam sheet and is provided with a neck opening 34, the neck opening in the sheet fitting the 5 to 95 percentile adult population (11.8 to 16.6 inch neck circumference). The periphery of foam sheet 14 is secured to an inner surface of the film strip 32 by a urethane adhesive.

Figure 2:
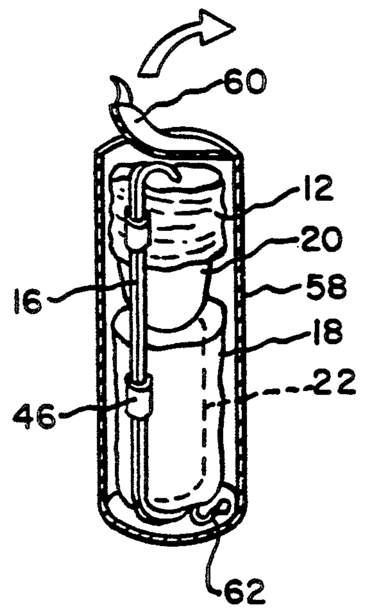
FIG. 2 illustrates how the quick-donning protective hood assembly of this invention may be packaged in a storage container.

The scrubber canister 20 may be of the type shown in FIG. 2 of copending U.S. application Ser. No. 07/403,303 filed Sep. 1, 1989. This form of scrubber canister includes a sorbent bed 36, filter 38, and venturi ejector 40 or pump which causes gas from the hood to be recirculated through the scrubber for the purpose of removing the wearer's exhaled carbon dioxide. The sorbent bed 36 includes anhydrous lithium hydroxide which is also capable of absorbing many toxic acid gases that may be introduced into the hood during donning. As the scrubber canister is more fully described in the foregoing U.S. patent application, the subject matter of which is incorporated herein by reference, it will not be described in greater detail. The hood is also provided with an exhaust valve 42 of conventional construction.

Figure 1:
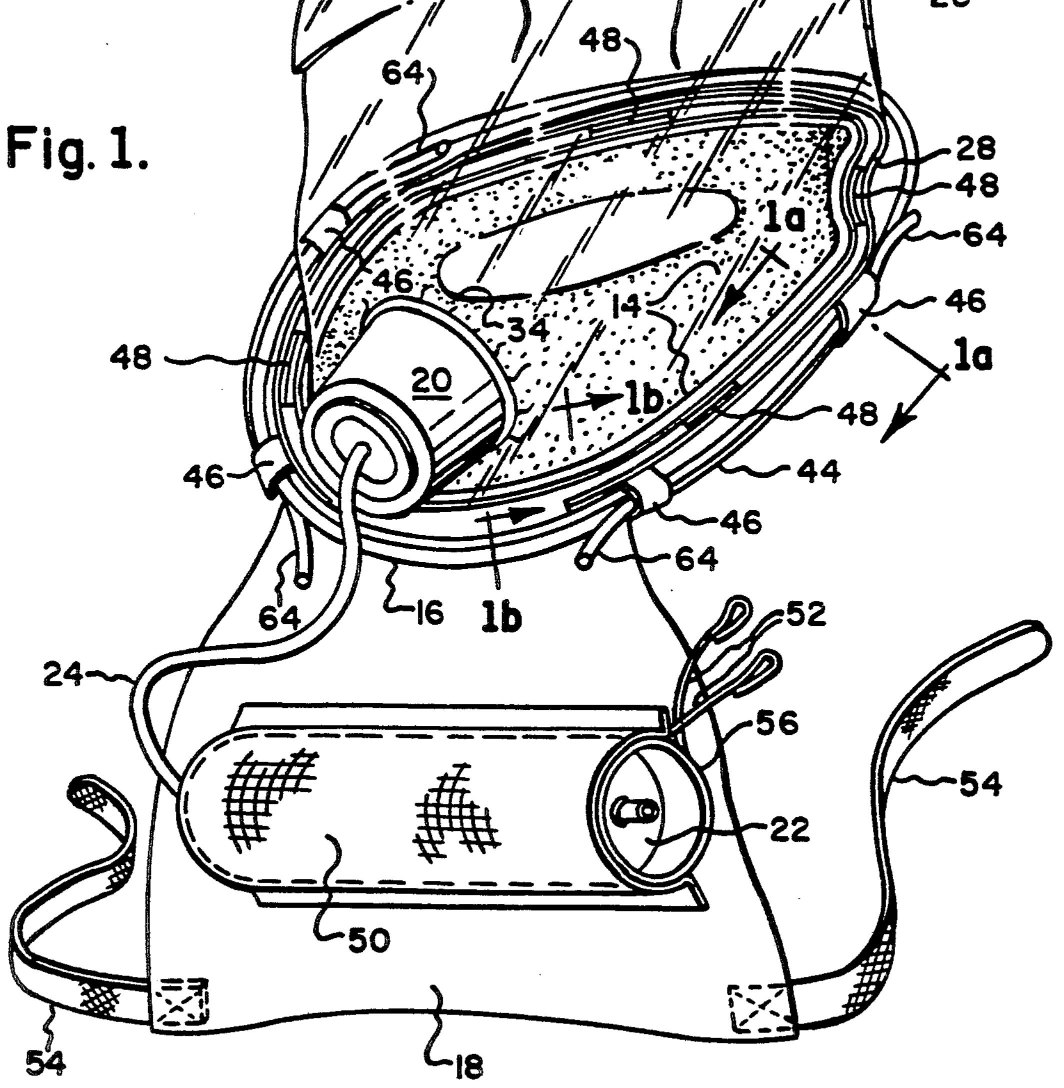
FIG. 1 is a perspective view of the quick-donning protective hood assembly of this invention.
Figure 4:
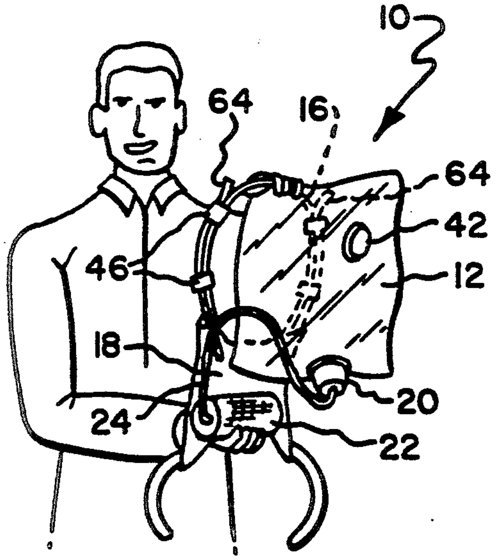
FIG. 4 shows the assembly of this invention ready for donning.
Figure 5:
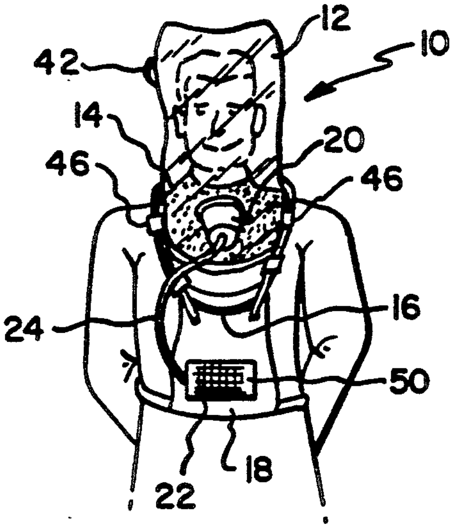
FIG. 5 illustrates how the quick-donning protective hood assembly of this invention may be worn.
Figure 6:
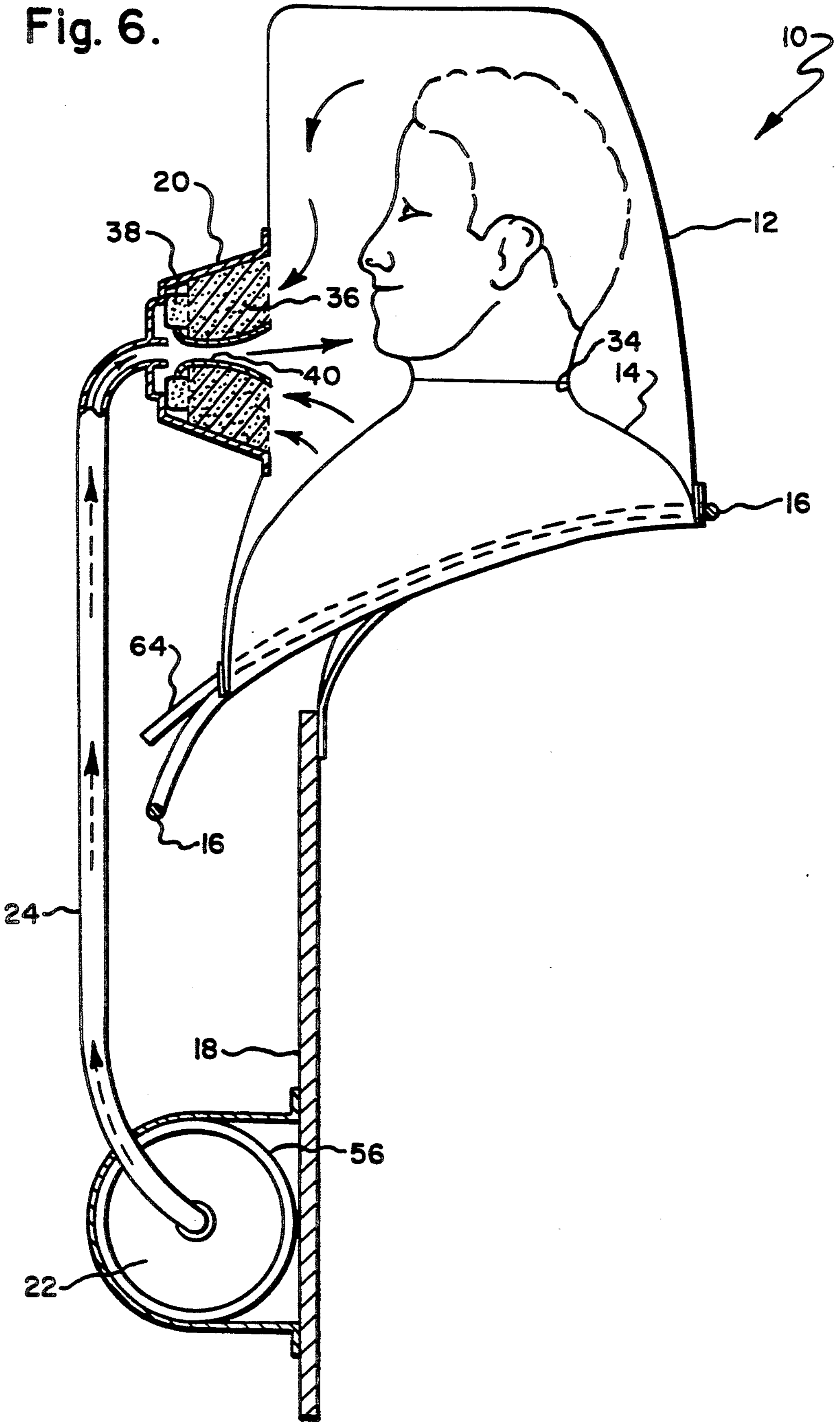
FIG. 6 is a side-sectional view of the assembly of the present invention, showing the position of the parts if the assembly were donned as shown in FIG. 5.

The springlike neck hoop 16 is disposed outside of the tape 30, the neck hoop being capable of being collapsed in the manner indicated in FIG. 2 when it is placed in a storage container. When the assembly of this invention is removed from the storage container, the neck hoop will spring open to a generally circular configuration as indicated in FIGS. 1, 4, and 5. A fabric tape 44 extends along the sides and back of the neck hoop, the tape 44 having sewn thereon elongated fabric elements 46 in the nature of belt loops, the hoop passing through the belt loops. Hook and loop pile fasteners, such as the type sold under the tradename "VELCRO", are secured to spaced apart locations of the fabric tape 44 and also to the tape 30 so that the neck hoop may be secured to the lower end of the hood 12. The ends of the fabric tape 44 are sewn to the top edge of the bib 16 so that the bib is supported by the neck hoop.

A generally cylindrical tubular nylon mesh element, provided with drawstrings 52 at one end is sewn or otherwise secured to the bib 18. In addition, the bib is also provided with waist straps 54. The oxygen generator is held in the nylon bib by drawing tight the drawstrings 52, the generator being within an insulated heat shield 56 concentric with the generator to protect the wearer from excess heat.

The springlike hoop may be formed of differing materials. Thus, it may be plastic or alternatively it may be a composite including a spring wire.

The sides of the neck hoop may be positioned parallel to each other with the generator 22, canister 20, and hood 12 positioned between the sides when stored in a storage container 58. The neck hoop will expand when withdrawn from a storage container 58. Thus, if a spring wire is utilized, the spring wire in the neck hoop will cause the hood and bib to assume their unfolded shape when the neck hoop is pulled from its storage container 58 as indicated in FIG. 4, the unfolding facilitating donning.

Figure 3:
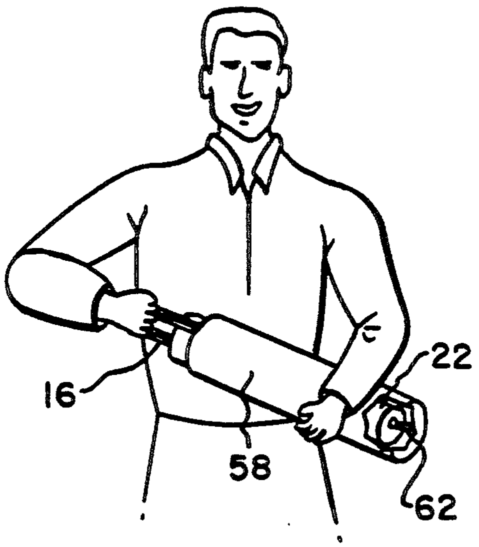
FIG. 3 illustrates how the assembly may be withdrawn from the storage container.

The protective hood assembly of this invention is preferably stored for use in a cylindrical canister 58 with a pull-type foil cover 60. When it is desirable to utilize the protective hood assembly, it is necessary to first remove the cover 60 by pulling as indicated by the arrow in FIG. 2. This will expose one end of the neck hoop which will then be engaged by one hand of the user, the other hand of the user holding the canister as illustrated in FIG. 3. As the unit is withdrawn from the container, a firing lanyard 62 will automatically actuate the oxygen generator 22 as the unit is removed from its storage container. One end of the lanyard being secured to the inside of the base of the storage container 58 and at the other end to the oxygen generator. Thus, the chemical production of oxygen by the oxygen generator is automatically initiated by a percussion cap when the unit is removed from the storage container. Oxygen will now flow at a set flow rate to the scrubber canister where the oxygen powers the venturi ejector or pump. The venturi causes gases to be recirculated from the hood through the scrubber where the passenger's exhaled carbon dioxide is removed. The oxygen generator is preferably designed to produce an initial high oxygen flow rate immediately after donning to purge the hood 12 and fill it with a respirable gas. The vent valve or exhaust valve 42 in the hood allows excess oxygen to escape to the atmosphere.

It is an additional feature of the present invention to provide one or more chemiluminescent devices which are connected to the hood assembly, the operation of the devices being initiated when the protective hood assembly is withdrawn from the storage container to facilitate the donning of the device, particularly when dark. Such devices may also be used for finding the wearer by rescue personnel. While various such devices may be utilized, a preferred form of the device is a CYALUME light stick manufactured by the American Cyanamid Company, Chemical Light Department, 1 Cyanamid Plaza, Wayne, N.J. 07470. These devices when bent will initiate a chemiluminescent reaction. A pair of light sticks 64 may be mounted on the sides of the hoop 16, as shown in FIG. 2, with each light stick passing through a pair of loops 46. Thus, at least two light sticks may be mounted onto the hoop 16 when it is compressed in its storage position, the sticks being mounted without initiating the chemiluminescent reaction. When the protective hood assembly is withdrawn from the canister, the chemiluminescent reaction will be initiated providing suitable lighting to facilitate donning and finding of the wearer by rescue personnel. While the use of CYALUME light sticks is presently contemplated, it should be appreciated that other chemiluminescent devices may be developed in the future which may also have application to the present invention.

While a preferred construction in which the principles of the present invention have been incorporated are shown and described above, it is to be understood that the present invention is not to be limited to the particular details, shown and described above, but that, in fact, widely differing means may be employed in the practice of the broader aspects of this invention.

What is claimed is:

1. A quick-donning protective hood assembly for respiratory protection from smoke and noxious gases; the hood assembly comprising:

a hood capable of being donned over a head, the hood having an open lower marginal portion;

a neck seal carried by the lower marginal portion of the hood, the neck seal being capable of engaging the neck of a user when the hood is donned over the head of the user;

a springlike neck hoop connected to the lower marginal portion of the hood, the neck hoop being in a collapsed state when stored within a storage container, the neck hoop springing into an open hoop when withdrawn from the storage container to facilitate donning of the hood and neck seal about the head; and one or more chemiluminescent devices connected to the hood assembly, the operation of said devices being initiated when the protective hood assembly is withdrawn from the storage container.

2. The protective hood assembly as set forth in claim 1 wherein the chemiluminescent devices are light sticks secured to the neck hoop, which sticks will be bent during withdrawal of the assembly, the bending of the sticks initiating a chemiluminescent reaction.

3. A protective assembly comprising, in combination:

a cylindrical storage container; and a quick-donning protective hood assembly for respiratory protection from smoke and noxious gases, said assembly being initially stored prior to use in said storage container, the hood assembly including a hood capable of being donned over a head, the hood having an open lower marginal portion, a neck seal carried by the lower marginal portion of the hood, the neck seal being capable of engaging the neck of a user when the hood is donned over the head of the user, a springlike neck hoop connected to the lower marginal portion of the hood, the neck hoop being in a collapsed elliptical state when stored within the storage container and providing a handle means for removal of the hood assembly from the storage container, the neck hoop being capable of springing into an open hoop when the quick-donning protective hood assembly is withdrawn from the storage container to facilitate donning of the hood and neck seal about the head, and an oxygen generator for supplying oxygen to the hood when the operation of the generator is initiated; and means including a lanyard which is secured to the inside of the storage container and which is also secured to the oxygen generator for causing the operation of the oxygen generator to be initiated when the quick-donning protective hood assembly is withdrawn from the storage container.

4. The assembly as set forth in claim 3 further being characterized by the provision of of a bib secured to the neck hoop, the oxygen generator being carried by the bib.

5. The assembly as set forth in claim 4 wherein the bib carries a pair of waist straps which are adapted to be placed about the waist of the wearer to secure the bib in place.

6. The assembly as set forth in claim 4 further being characterized by the provision of a scrubber canister being mounted on an exterior portion of the hood, the scrubber canister including a venturi pump, and wherein an oxygen supply line extends from the oxygen generator to the scrubber canister.

7. A protective assembly comprising, in combination, an elongate storage container and a quick-donning protective hood assembly for respiratory protection from smoke and noxious gases, the hood assembly being stored prior to use in said storage container, the hood assembly comprising:

a hood capable of being donned over a head, the hood having an open lower marginal portion;

a scrubber canister carried by an external surface of the hood, the scrubber canister being provided with a venturi pump, and the scrubber canister being capable of removing carbon dioxide from air;

elongate means providing a source of oxygen and inserted prior to use longitudinally in said storage container and connected to the venturi pump to cause the venturi pump to recirculate exhaled air through the scrubber canister for the removal of carbon dioxide;

a neck seal carried by the lower marginal portion of the hood, the neck seal being capable of engaging the neck when the hood is donned over the head; and a springlike neck hoop connected to the lower marginal portion of the hood, the neck hoop being in a collapsed elliptical state when stored within the storage container and providing a handle means for removal of the hood assembly from the storage container, the neck hoop springing into an open hoop when withdrawn from the storage container to facilitate donning of the hood and neck seal about the head.

* * * * *